(12) United States Patent
Kuepper et al.

(10) Patent No.: US 6,323,032 B1
(45) Date of Patent: *Nov. 27, 2001

(54) STERILIZER TESTING SYSTEMS

(75) Inventors: Anton Kuepper, Kaarst (DE); Brian Kirk, Derbyshire (GB)

(73) Assignee: 3M Innovative Properties Company, St. Paul, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/043,390

(22) PCT Filed: Oct. 7, 1996

(86) PCT No.: PCT/US96/16054

§ 371 Date: Mar. 17, 1998

§ 102(e) Date: Mar. 17, 1998

(87) PCT Pub. No.: WO97/12637

PCT Pub. Date: Apr. 10, 1997

(51) Int. Cl.[7] .............................. G01N 30/54; A61L 2/24

(52) U.S. Cl. .................................. 436/1; 436/3; 422/26; 422/109; 422/110

(58) Field of Search ................................ 436/1–3, 6–7; 422/26, 298, 109–111, 116

(56) References Cited

U.S. PATENT DOCUMENTS

| | | | |
|---|---|---|---|
| 3,982,893 | * | 9/1976 | Joslyn ................................ 422/56 |
| 4,309,381 | * | 1/1982 | Chamberlain et al. ............... 422/56 |
| 5,063,297 | | 11/1991 | Hardenbrook et al. ........... 250/458.1 |
| 5,422,276 | | 6/1995 | Colvin ..................................... 436/1 |
| 5,491,092 | | 2/1996 | Colvin ..................................... 436/1 |
| 5,565,634 | | 10/1996 | Graessle et al. .................... 73/865.9 |

FOREIGN PATENT DOCUMENTS

| | | |
|---|---|---|
| 14 92 398 | 3/1964 | (DE) . |
| 43 19 398.6-41 | 10/1994 | (DE) . |
| 0 290 929 | 11/1988 | (EP) . |
| 0 419 282 B1 | 7/1993 | (EP) . |
| 0 607 941 A2 | 7/1994 | (EP) . |
| WO94/28946 | 12/1994 | (WO) . |
| WO94/28947 | 12/1994 | (WO) . |
| WO 97/12637 | 4/1997 | (WO) . |
| WO 98/33286 | 7/1998 | (WO) . |

* cited by examiner

Primary Examiner—Lyle A. Alexander
(74) Attorney, Agent, or Firm—John A. Burtis

(57) ABSTRACT

A sterilant challenge device, for use in testing the efficiency of the removal stage of a sterilization cycle in a sterilizer. In a preferred embodiment, the device includes a tube that is closed at one end and open at the other for the entry of sterilant, a plurality of thermally-conductive masses the tube, and at least one temperature sensor. When the challenge device is located in a sterilizer, the penetration of sterilant along the bore of the tube during a sterilization cycle, is inhibited by the accumulation of air and/or non-condensable gas within the bore resulting from the condensation of moisture on the walls of the bore. By measuring the temperature inside the device adjacent the closed end of the tube, the efficiency of the sterilization cycle can be determined.

12 Claims, 6 Drawing Sheets

STERILIZER TESTING SYSTEMS

CROSS REFERENCE TO RELATED APPLICATION

This application claims priority to PCT International Patent Application No. PCT/US96/16054, filed Oct. 7, 1996 which claims priority to European Patent Application No. 95202692.0 filed Oct. 6, 1995.

FIELD

The present invention relates to stem and methods for determining the efficacy of sterilization cycles in sterilizers.

BACKGROUND

A sterilization process used to sterilize medical and hospital equipment is only effective if a certain combination of environmental conditions is achieved within the sterilization chamber of the sterilizer. For example, when steam is used as a sterilant, the object of the sterilization process is to bring steam of a suitable quality, and at an appropriate temperature into contact with all surfaces of the articles being sterilized for a correct length of time In some steam sterilizers the process of sterilization is typically conducted in three main phases. In the first phase, air trapped within the load being processed is removed. The second phase is a sterilizing stage, in which the load is subjected to steam under pressure for a recognised combination of time and temperature, which is known to effect sterilization. The third phase is a drying phase in which condensate formed during the first two phases is removed by evacuating the chamber.

Air removal from the sterilization chamber may be achieved in a number of ways. For example, in a gravity steam sterilizer, the principle of gravity displacement is utilized, in which steam entering at the top of the chamber displaces the air through a valve in the base of the chamber. In a prevacuum steam sterilizer, on the other hand, air is removed forcibly by deep evacuation of the chamber or by a combination of evacuation and steam injection at either subatmospheric and/or superatmospheric pressures.

Any air which is not removed from the sterilization chamber during the air removal phase of the cycle or which leaks into the chamber during a subatmospheric pressure stage due to faulty gaskets, valves or seals, may form air pockets within the load that is being sterilized. Likewise, any non-condensable gases (which, in this context, means gases having a boiling point below that of the sterilant) that are present in the sterilization chamber or are carried within steam supplied to the chamber may form gas pockets within the load. These air or gas pockets will create a barrier to steam penetration, thereby preventing adequate sterilizing conditions being achieved for all surfaces of the load. This is particularly true when porous materials such as hospital linens or fabrics are being sterilized since the air or gas pockets prohibit the steam from penetrating to the interior layers of such materials. As a result, sterilization may not occur. Therefore, there is a need to be able to determine the efficacy of sterilization cycles and in particular, to determine whether there has been sufficient steam penetration. Similarly, when a sterilant other than steam is used, there is a need to be able to determine that the sterilant has penetrated a load sufficiently for sterilization to take place.

One commonly-used procedure for evaluating the effectiveness of air removal during the air removal phase of a porous load steam sterilization cycle and/or for testing for the presence of non-condensable gases is known as the Bowie-Dick test. The typical Bowie-Dick test pack essentially consists of a stack of freshly laundered towels folded to a specific size, with a chemical indicator sheet placed in the centre of the pack. Chemical indicator test sheets undergo a visible change from one distinct colour to another, for example, from an initial white to a final black colour, upon exposure to the sterilization process. If the air removal within the sterilizer is insufficient, or if non-condensable gases are present during the process in sufficient quantity, an air/gas pocket will form in the centre of the pack thereby preventing steam from contacting the steam sensitive chemical indicator sheet. The consequence of inadequate steam penetration is a non-uniform colour development across the surface of the chemical indicator test sheet: thus, the presence of the air/gas pocket will be recorded by the failure of the indicator to undergo the complete or uniform colour change indicative of adequate steam penetration.

Biological indicators can also be used to provide information on the adequacy of a sterilization cycle. Biological indicator test systems typically employ living spores which are subjected to a sterilization cycle. After the cycle, the spores are incubated and the system detects if there is any growth. If there is no growth, it indicates that the sterilization process has been effective. Thus, biological indicators can determine whether conditions for sterilization were present, but the length of time to obtain results due to the incubation period is often at least 24 hours. Therefore, biological indicator systems are often used in conjunction with chemical indicators because the colour change of the chemical indicators provides an instant result. Further, by using both chemical and biological indicators, information on both the adequacy of the air removal stage and the sterilization stage is provided.

Parametric monitoring has also been used to either monitor or control a sterilization cycle to ensure proper sterilization conditions are attained. For example, in U.S. Pat. No. 4,865,814 to Childress, an automatic sterilizer is disclosed which includes a microprocessor which monitors both the temperature and pressure levels inside the sterilization chamber and controls a heater to allow both pressure and temperature to reach predetermined levels before starting a timer. Once the timer is started, it is stopped if the pressure or temperature levels drop below a predetermined minimum. Since it is known that the pressure and temperature variables of saturated steam are dependent variables when saturated steam is enclosed in a sealed chamber, monitoring of these two variables can ensure that proper conditions are maintained during the sterilization cycle.

Although it is desirable to monitor environmental conditions within the sterilization chamber itself, it is generally considered more desirable to be able to monitor the environmental conditions within an actual load being sterilized or within a test pack (such as the Bowie-Dick test pack) that represents such a load. Although the typical Bowie-Dick test pack is generally recognized as adequate for use in determining the efficacy of the air removal stage of prevacuum sterilizers, it still presents many disadvantages. Since the test pack is not preassembled, it must be constructed every time the procedure is used to monitor sterilizer performance. The preparation, assembly and use of the towel pack is time consuming and cumbersome and, moreover, varying factors, such as laundering, prehumidification, towel thickness and wear, and the number of towels used, alter the test results. Therefore, alternative Bowie-Dick test packs have been developed to overcome these limitations.

An example of an alternative Bowie-Dick test pack for steam or gas sterilizers is described in EP-A-0419282. That test pack includes a container having top and bottom walls with a porous packing material disposed within the container. The packing material challenges the penetration of the sterilant by providing a restricted pathway which acts to impede the flow of the sterilant through the test pack. A removable lid seals the bottom end of the container, while a hole in the top wall of the container allows for the downward ingress of steam into the packing material within the container. The test pack includes a chemical indicator for detecting sterilant penetration. If sterilant successfully penetrates the packing material of the test pack, the chemical indicator sheet will undergo a complete colour change. If the sterilant does not sufficiently penetrate the packing material, the chemical indicator will not undergo a complete uniform colour change, thereby indicating inadequate air removal or the presence of non-condensable gas, or in other words, a Bowie-Dick test failure.

Other test packs for use in steam or gas sterilizers are described in EP-A-0 421 760; U.S. Pat. No. 5,066,464; WO 93/21964 and U.S. Pat. No. 5,270, 217. In each of those test packs, sterilant from the sterilization chamber must cross some form of physical barrier before it reaches a sterilant sensor within the test pack. WO 93/21964, for example, describes a test unit comprising a test cavity having an opening at one end to permit entrance of ambient gases, a temperature sensor at the other end and a heat sink (for example gauze, felt, open-celled polymer foam) between the temperature sensor and the opening.

U.S. Pat. No. 4,594,223 describes various devices for indicating the presence of non-condensable gas in a sterilization chamber. In one version, a heat and humidity sensor is located at the lower end of an elongate cavity which is open at the upper end. Heat sink material in the form of fibrous insulating material is located within the cavity between the opening and the sensor. In another version, the path between the opening and the sensor is through a heat sink block in the form of a mass of aluminum surrounded by insulation, rather than through fibrous heat sink material. U.S. Pat. No. 4,115,068 describes an air indicating device for use in sterilizers, comprising an upright tube which is open at its bottom end and closed at its top end. The tube is made of heat insulating material lined on its interior surface with a heat conducting material. A thermal indicator strip extends axially into the tube.

Another known arrangement for challenging the penetration of sterilant to a particular location within a test pack comprises a very long (typically, 1.5 m) stainless steel tube with a narrow bore (typically, 2.0 mm) which provides the only access for sterilant to the predetermined location.

SUMMARY OF THE INVENTION

The problem with which the present invention is concerned is that of providing, for sterilizer testing systems, a sterilant challenge device which is of comparatively simple construction but which will function reliably to enable ineffective sterilization cycles to be identified.

The present invention provides a sterilant challenging device for use in a sterilizer for determining the efficiency of the air removal stage of a sterilization cycle, the device comprising a chamber defining a free space; an opening for the entry of sterilant to the free space; a heat sink portion which, when the device is in use in a sterilizer, receives heat preferentially from the free space; and means for mounting a sensor to detect the presence of sterilant at a predetermined location within the free space remote from the said opening, the walls of the chamber comprising a thermally insulating material which impedes the transmission of heat from within the sterilizer to the free space through the walls of the chamber whereby the penetration of sterilant from the said opening to the said predetermined location during a sterilization cycle is inhibited by the accumulation of air and/or non-condensable gas within the free space resulting from the condensation of moisture on the walls of the chamber.

The device may be provided with a sensor for detecting the presence of sterilant at the predetermined location. The sensor may comprise a temperature sensor for detecting the temperature at the predetermined location. Alternatively, or in addition, the sensor may comprise a humidity sensor for detecting the presence of moisture at the predetermined location. Alternatively, or in addition, the sensor may comprise a biological/chemical sensor for detecting the presence of sterilant at the predetermined location.

The heat sink portion may be surrounded by a thermally-insulating portion whereby, during a sterilization cycle, the heat sink portion will receive heat preferentially from the free space.

The chamber may comprise a passageway which is closed at one end, the predetermined location being towards the closed end of the passageway, and the opening for the entry of sterilant being at the other end of the passageway. The passageway may be the bore in a tube of thermally-insulating material and the heat sink portion may comprise a plurality of thermally-conductive masses located around the tube along the length of the latter, the masses being thermally-separated from each other. Alternatively, the passageway may be formed in a mass of thermally-insulating material; in that case, an inner part of the mass of thermally-insulating material forms the heat sink portion of the device and an outer part functions as a thermally-insulating portion whereby, during a sterilization cycle, the heat sink portion will receive heat preferentially from the free space.

Alternatively, the passageway may comprise a plurality of interconnecting compartments. In the latter case, the compartments may be linearly-arranged, the opening for the entry of sterilant being in the compartment at one end of the linear arrangement, and the predetermined location being in the compartment at the other end of the linear arrangement. Alternatively, the compartments may be arranged so that one, at least, of the compartments is surrounded by others, the opening for the entry of sterilant being in a compartment at the periphery of the arrangement, and the predetermined location being in a compartment at the centre of the arrangement. A heat sink portion of the device may comprise heat sink masses within the compartments.

The present invention also provides a sterilant challenge device for use in a sterilizer for determining the efficiency of the air removal stage of a sterilization cycle, the device comprising a tube of thermally-insulating material, the bore of the tube defining a free space which is open at one end for the entry of sterilant and is closed at the other end; a plurality of thermally-conductive masses located around the tube, along the length of the latter, the masses being thermally-separated from one another; and thermal insulation surrounding the tube and thermally-conductive masses whereby the penetration of sterilant along the bore of the tube during a sterilization cycle is inhibited through the accumulation of air and/or non-condensable gas within the free space resulting from the condensation of moisture on the walls of the bore, the device also comprising means for mounting a sensor to detect the presence of sterilant at, or adjacent, the closed end of the tube. The device may be used in combination with a second temperature sensor positioned to detect the temperature in a sterilization chamber in which the device is located.

BRIEF DESCRIPTION OF THE DRAWINGS

By way of example only, embodiments of the invention will now be described with reference to the accompanying drawings, in which.

DETAILED DESCRIPTION

Figure 1:
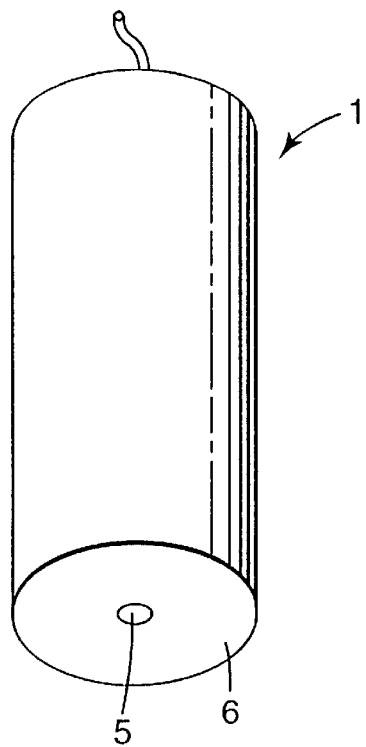
FIG. 1 is a perspective view of a sterilant challenge device in accordance with the invention.
Figure 2:
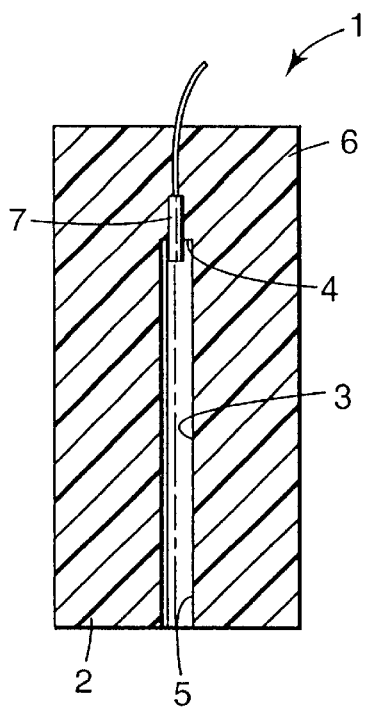
FIG. 2 shows a longitudinal cross-section of the device of FIG. 1.

FIGS. 1 and 2 show a sterilant challenge device I suitable for use in a system for testing the efficacy of a sterilization cycle in a steam sterilizer or in a low temperature gas sterilizer in which sterilization is carried out using a microbiocidal agent in the presence of moisture. The device 1 is intended to be located in the sterilization chamber of the sterilizer to provide a challenge path along which sterilant (for example, steam) from within the chamber must pass before it can be detected by a sensor at a predetermined location within the device. If the presence of sterilant at the predetermined location is not detected by the sensor during a sterilization cycle (indicating that the conditions within the sterilization chamber have not enabled sterilant to penetrate the challenge path), the sterilization cycle is judged to be ineffective. The challenge device 1 is generally cylindrical and comprises a tube 2, with a bore 3 of generally constant cross-section, which is closed at one end 4 and open at the other end 5. The wall 6 of the tube 2, which is comparatively thick, is formed of a thermally-insulating material and has a comparatively high heat capacity. A sterilant sensor 7 of any suitable type is located at the closed end 4 of the tube.

In use, the challenge device 1 is located in the sterilization chamber of a sterilizer with the bore 3 connected, through the open end 5, to the environment within the sterilization chamber. The device is used in the orientation shown in the drawings, i.e. with the open end 5 of the bore 3 directed downwards, so that any condensate which forms within the bore can drain away. Depending on the thermal properties of the tube 2, it has been found that a pocket of air or non-condensable gas will tend to remain at the closed end 4 of the bore 3 during an inadequate sterilization cycle and will inhibit the entry of sterilant. Accordingly, by appropriate selection of the thermal properties of the tube, it can be arranged that sterilant will not penetrate to that end of the bore when the environmental conditions in the sterilization chamber do not satisfy the requirements for effective sterilization. Detection of sterilant by the sensor 7 is then an indication that a sterilization cycle has been effective while non-detection is an indication that a sterilization cycle has failed to meet requirements.

In general, the thermal properties of the tube 2 should be such that heat and moisture from the sterilization chamber will pass to the sensor 7 through the bore 3 rather than through the walls 6 of the tube (with the result, in the case of a steam sterilizer, that steam which passes into the bore 3 will tend to condense on the walls of the bore and not penetrate immediately to the sensor). In the case of the device shown in FIG. 1, it will be noted that the inner surface of the wall 6 of the bore 3 comprises, like the rest of the device, a thermally insulating material. Moreover, if the wall of the bore is sufficiently thick, the inner part of the mass of thermally-insulating material will function as a heat sink portion which, in use, will receive heat preferentially from the bore 3 because it is surrounded by an outer part of the thermally-insulating material which impedes the transfer of heat from the sterilizer across the wall of the bore in a transverse direction.

It will be noted that the device 1 does not require the presence of any form of packing material, or other physical barrier, within the bore 3 to inhibit the penetration of sterilant to the sensor 7. The tube is also comparatively short (typically, with a bore length of less than 30 cm, preferably less than 20 cm, and most preferably less than 10 cm) and, accordingly, does not rely on length to impede the penetration of sterilant to the sensor 7. Indeed, it has been found that a device with a bore length of 7.5 cm can provide an indication of the efficacy of a sterilization cycle. The bore 3 functions as an enclosed chamber defining a free space which separates the sensor 7 from the opening 5 and, as described above, it is the thermal properties of the surrounding walls 6 that cause the penetration of sterilant into the chamber to be inhibited and thus allow the device 1 to be used to indicate the efficacy of a sterilization cycle.

Suitable materials for the walls 6 of the tube 2 include polysulphone, polyphenylsulphone, polytetrafluoroethylene and polyetheretherketone. In general, it is believed that materials for which the ratio of thermal capacity to thermal conductivity is within the range of from $1 \times 10^6$ to $12 \times 10^6$ sec/m$^2$ (more particularly from $4 \times 10^6$ to $11 \times 10^6$ sec/m$^2$ are most suitable for the tube.

The outer diameter of the tube 2 is determined by the thickness of the walls 6 and the diameter of the bore 3, and is advantageously as small as possible consistent with the tube having the required thermal properties. The diameter of the bore 3 is also, advantageously, as small as possible but not so small that it can be blocked by condensate which forms within the bore during a sterilization cycle. It has been found that an indication of the efficacy of a sterilization cycle can be obtained with devices in which the outer diameter of the tube 2 is 5 cm or less and in which the diameter of the bore 3 is 0.9 cm or less (preferably 0.6 cm).

In some circumstances, it may be appropriate for the bore 3 to include means such as baffles for modifying the flow of air in the bore, for example to reduce turbulence. Any such means should be selected to ensure that the free space separating the sensor 7 from the bore opening 5 is retained and is not so constricted that it could be blocked by condensate during a sterilization cycle.

The sensor 7 may be a chemical indicator which changes colour in the presence of sterilant; or a biological indicator; or a sensor which detects an environmental parameter (for example, temperature or humidity). If required, several sensors could be employed. For example, a chemical indicator could be used in combination with a biological indicator, or sensors could be used to detect several environmental parameters (e.g. temperature, humidity and pressure).

Figure 7:
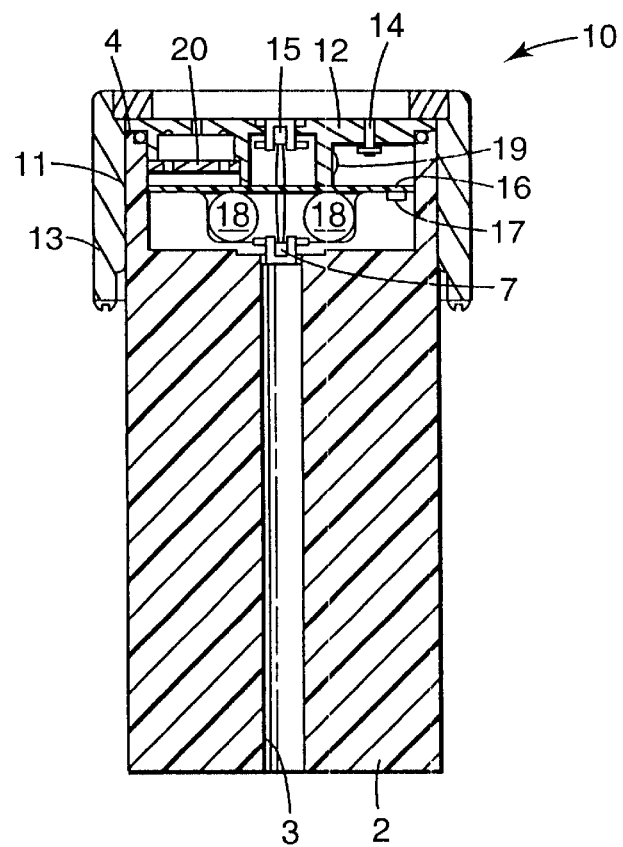
FIGS. 7 to 9 show diode cross-sections of test packs which incorporate challenge devices in accordance with the invention.

FIG. 7 illustrates one use of a challenge device of the type shown in FIGS. 1 and 2. FIG. 7 shows a cross-sectional view of a self-contained electronic test pack 10 which can be placed in a sterilization on chamber to determine the efficacy of a sterilization cycle. As described below, the test pack 10 functions, during a sterilization cycle, to measure the temperature at two locations, one being within the challenge device 1 and the other being at a reference point within the sterilization chamber itself. Those temperature measurements are then used to determine whether or not the sterilization cycle, in particular the air removal phase of the cycle, was effective (i.e. met certain prescribed requirements).

In the test pack shown in FIG. 7, the end wall 4 of the test pack 1 is hollowed-out to form a housing 11 which contains the electronic components of the test unit. Those components will be described below. The electronics housing 11 has a removable end cap 12 and is positioned within an outer housing 13 to which it secured, for example by screws. When secured, the outer housing 13 holds the end cap 12 to the electronics housing 11 so that the latter is sealed. Outer housing 13 is constructed of a structurally rigid material, such that when stressed, it returns to its original shape. For example, any type of metal as well as glass fiber or carbon fiber reinforced plastic with softening temperatures higher than 150° C. can be used for outer housing 13.

The components housed inside electronics housing 11 may be protected from the extreme heat within the sterilization chamber by a vacuum within the housing. To that end, electronics housing 11 includes one-way valve 14 which opens when the pressure external to the housing 11 falls below a predetermined value. Then, when a vacuum is pulled within a sterilization chamber with test pack 10 placed inside, valve 14 opens to allow a vacuum also to be pulled within electronics housing 11.

Electronics housing 11 contains the sensor 7 of the challenge device 1, (in this case, a temperature sensor), together with a second temperature sensor 15. Temperature sensors 7 and 15 may be any suitable type of temperature transducer, for example, thermocouples or thermistors. Temperature sensor 7 as already described, is positioned such that it measures the temperature at the end of the bore 3 of the challenge device 1. Temperature sensor 15, on the other hand, measures the external temperature. Thus, when electronic testpack 10 is placed within a sterilization chamber, temperature sensor 15 measures the chamber temperature.

Housing 11 also contains a circuit board 16, mounted so that it is thermally isolated from the walls of the housing to prevent conduction of external heat to the electronics mounted on the board, which include a microprocessor and a memory, preferably an electrically erasable programmable read-only memory (EEPROM). Surface mounted chips 17, batteries 18, the temperature sensors 7 and 15, a light emitting diode 19 and a pressure sensor 20 are all electrically connected to circuit board 16.

As temperature sensors 7 and 15 measure temperatures, the temperature readings are stored in the test pack memory together with time data from the microprocessor. Once the microprocessor determines that a sterilization cycle is complete, it then determines (from the stored temperature readings) whether the sterilization cycle is satisfactory, in other words, that the sterilant has adequately penetrated the length of the bore 3 in the challenge device.

If the microprocessor determines that the sterilization cycle was satisfactory, light emitting diode (LED) 19 emits light. In a completely self-contained electronic test pack, only a single LED is necessary to indicate whether the cycle has passed. With a single LED, the LED may continuously burn to indicate a pass cycle and may flash to indicate a fail cycle. Alternatively, two LEDs may be used, to indicate a pass cycle and fail cycle respectively. If the sterilization cycle has passed, one LED emits a green light. If the microprocessor determines that the sterilization cycle has failed, the other LED emits a red light.

In some situations, it is desirable to transfer the data stored in the memory of the unit to an outside processor or memory or a printer. Data transfer may be initiated by actuating a magnetically actuated switch (not shown), preferably a reed switch.

The manner in which the test pack 10 determines the efficiency of a sterilization cycle is, briefly, as follows. As already described with reference to FIG. 1, the thermal properties of the challenge device 1 are such that, during the air removal phase of a sterilization cycle, an air pocket will tend to remain at the inner (closed) end of the bore 3. Similarly, non-condensable gases carried by the steam will also tend to remain at the inner end of the bore 3. The size of the air/gas pocket is indicative of the efficiency of the sterilization cycle, being larger when the air removal phase of the cycle is less adequate. The air/gas pocket prevents the sensor 7 from being exposed to the full effects of sterilant, thus giving rise to a difference between the temperature at the sensor 7 and the temperature at the sensor 15. The test pack 10 determines if that temperature difference exceeds a predetermined value at a predetermined point within the sterilization cycle and, if so, the cycle is judged to be unsatisfactory. This predetermined temperature difference is determined by validation experiments in which the performance of the electronic test pack is compared with that of a standard Bowie-Dick textile test pack according to recognized International, European or National standards. For example, the test pack could be pre-programmed so that, if the temperature difference is greater than 2° C. in a 2 minute and 40 seconds period after the chamber temperature reaches a sterilization hold temperature of 134° C., the cycle is considered unsatisfactory. Further, the chamber temperature must remain above an adequate sterilization temperature for sterilization to occur.

While the examination of the temperature difference between the external and internal temperature (as just described) provides direct information on the penetration of heat to the sensor 8 located within the challenge device 1, it does not directly reflect penetration of sterilant to the sensor. By inference, rapid equilibrium between the sensing point within the challenge device and the sterilization chamber indicates the absence of an insulating air/gas pocket. In the case of a steam sterilizer, it is possible, however, to measure directly the moisture penetration to the sensing point within the challenge device. To that end, a moisture sensor, such as a conductivity sensor or a relative humidity sensor, can be used instead of or in addition to, the temperature sensor 8 to determine adequate moisture penetration to the sensing point within the challenge device and therefore, by inference, steam. The temperature sensor 15 measuring the sterilization chamber temperature remains the same.

Figure 3:
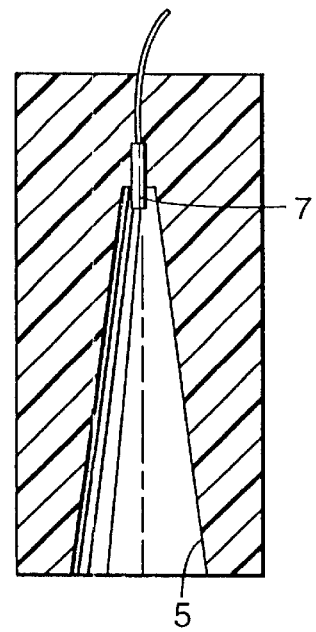
FIGS. 3 to 6 show diagrammatic cross-sections of other challenge devices in accordance with the invention.

FIG. 3 shows an alternative form of challenge device, similar to that shown in FIGS. 1 and 2 except that the cross-section of the bore 3 decreases towards the sensor 7.

Figure 4:
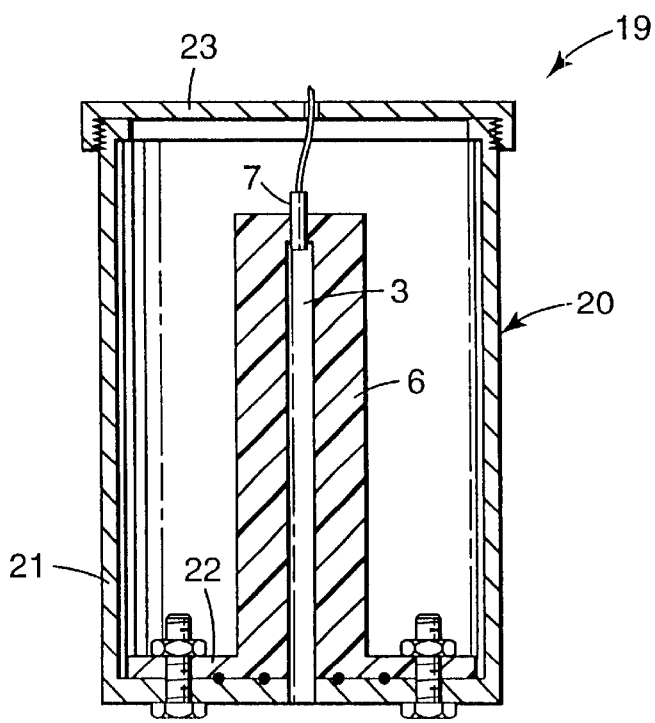

FIG. 4 shows a challenge device 24 in which the wall 6 of the bore 3, (although still formed from a thermally-insulating material) is thinner than in FIGS. 1 and 2, with additional thermal insulation being provided by air trapped between the wall 6 and a surrounding outer casing 25. The outer casing 25 need not be formed from a thermally-insulating material and could, for example, be metal. The outer casing 25 is formed in two parts, one of which (21) is secured and sealed to a flange 22 around the mouth of the bore 3. The second part 23 of the casing 20 is an end cap and is screwed to the first part so that it can be removed to give access to the sensor 7 at the closed end of the bore 3. The interface between the two parts 21, 23 of the casing 20 is also sealed.

In the challenge device shown in FIG. 4, the space 26 between the wall 6 and the outer casing 20 may contain some form of thermally-insulating filler material for example a thermally-insulating foamed material or glass wool. Alternatively, the space may be evacuated.

The construction illustrated in FIG. 4 enables a combination of different materials to be used and makes it possible to provide a challenge device which has the same thermal properties as the device shown in FIG. 1 but with smaller outer dimensions. In this construction, the wall 6 of the bore constitutes a heat sink portion of the device which, by virtue of the surrounding air space 26, will receive heat preferentially from the bore 3 when the device is located in a sterilizer.

Figure 8:
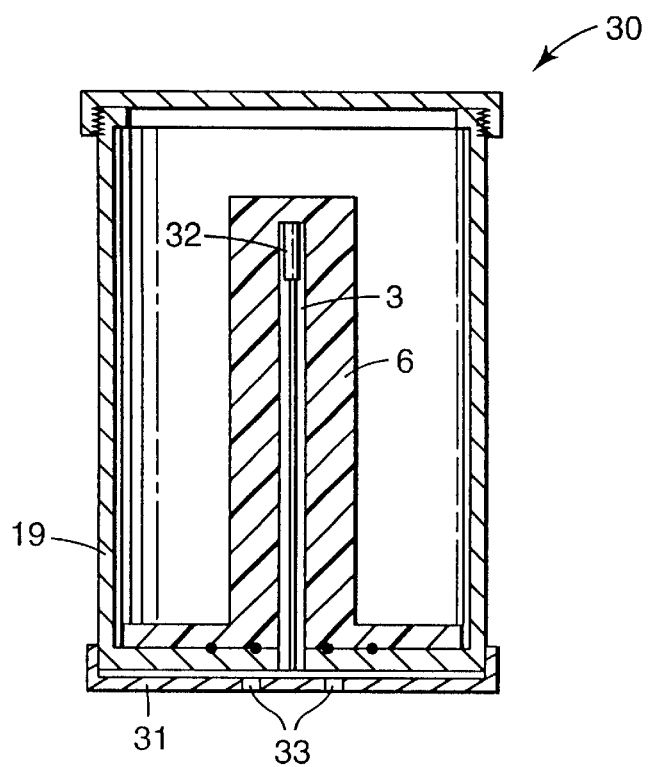
Figure 9:
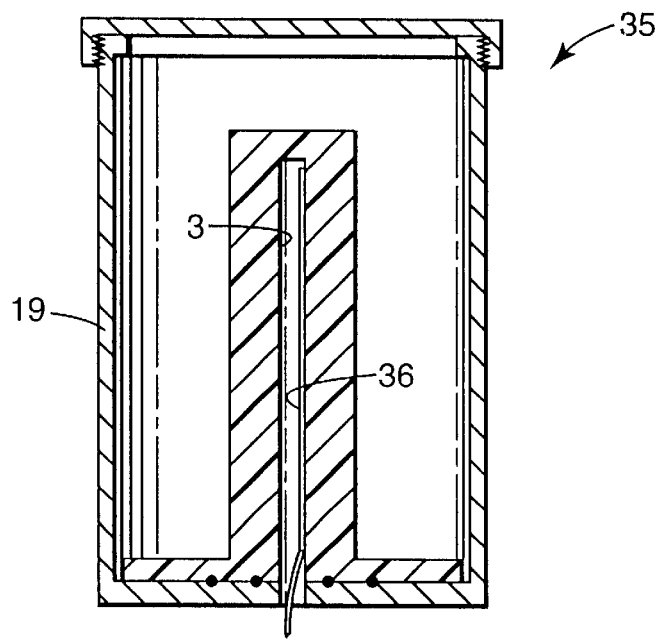

FIGS. 8 and 9 illustrate uses of a challenge device of the type shown in FIG. 4. FIG. 8 illustrates a test pack 30 which is formed by providing the challenge device 24 of FIG. 4 with a cap 31 which supports a biological indicator 32 so that when the cap 31 is fitted on the challenge device, over the open end of the bore 3, the indicator 32 is positioned at the closed end of the bore. The indicator 32 may be any suitable biological indicator, for example an indicator available under the trade designation "ATTEST" from Minnesota Mining and Manufacturing Company of St. Paul, Minn., U.S.A. The cap 31 has apertures 33 which allow sterilant to enter the bore 3 from outside the test pack 30.

The test pack 30 is intended to be placed in a sterilization chamber at the beginning of a sterilization cycle and to be removed when the cycle has been completed. The indicator 32 is then removed from the challenge device and subjected to the prescribed treatment to enable it to show whether or not the sterilization cycle was effective. The challenge device can, of course, then be fitted with a replacement indicator 32 and re-used.

FIG. 9 illustrates a test pack 35 which is similar to that shown in FIG. 8 except that it is provided with a chemical, rather than a biological, indicator. The chemical indicator is shown in the form of a strip 36 (comprising a substrate carrying a sterilant-sensitive ink) which extends along the length of the bore 3. A suitable chemical indicator is available under the trade designation "Comply 1250" from Minnesota Mining and Manufacturing Company of St. Paul, Minn., U.S.A.

The test pack 35 is also intended to be placed in a sterilization chamber at the beginning of a sterilization cycle and to be removed when the cycle has been completed. The indicator strip 36 is then removed from the challenge device and an examination of the colour change that has occurred along the length of the strip will immediately show how far sterilant has penetrated along the bore 3, and whether or not the sterilization cycle was effective. The challenge device can, of course, then be fitted with a replacement indicator strip 36 and re-used.

Figure 5:
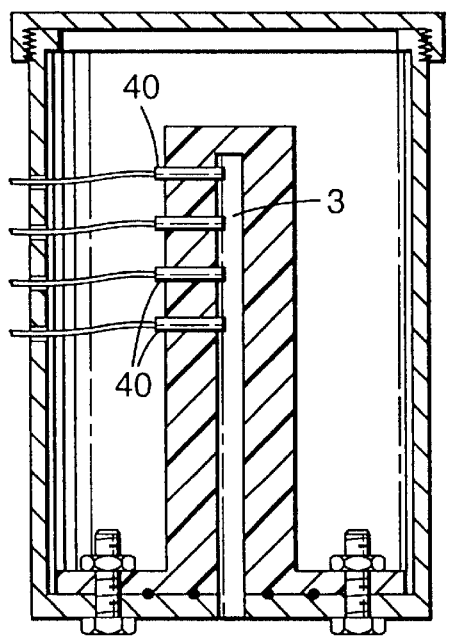

FIG. 5 shows another challenge device, similar to that shown in FIG. 4 but incorporating a plurality of sensors rather than just a single sensor. FIG. 5 shows four sensors 40, but any appropriate number could be used. The sensors 40 are located at different points along the length of the bore 3, with one being at the closed end of the bore and corresponding to the sensor 7 in FIG. 2. The parameters detected by the sensors 40 during a sterilization cycle will indicate how far sterilant has penetrated along the bore 3 of the challenge device at various times during the cycle and, in addition to indicating whether or not the sterilization cycle has been effective, can provide a record of sterilizer operation.

Figure 6:
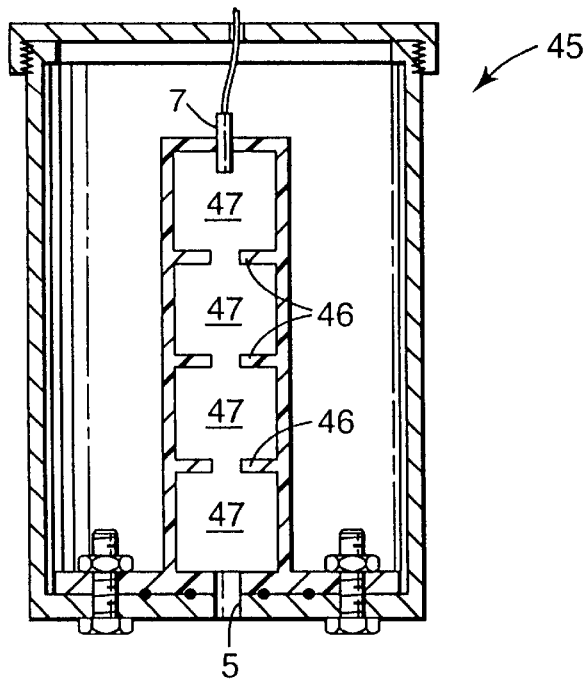

In each of the challenge devices shown in FIGS. 1 to 5, the walls of the bore 3 are straight and uninterrupted but that is not essential. The bore 3 could, for example, follow a helical path provided that adjacent turns in the path are thermally insulated from each other. Such an arrangement would enable the overall length of the challenge device to be reduced. As another alternative, a series of constrictions could be formed along the bore provided that none of those constrictions could be blocked by condensate during a sterilization cycle, and provided that they would not eliminate the free space separating the sensor 7 from the bore opening 5. An example of a challenge device of that type is illustrated in FIG. 6. The challenge device 45 shown in FIG. 6 is generally similar to that shown in FIG. 4 except for several apertured walls 46 at points along the length of the bore 3, which effectively divide the bore into a series of communicating compartments 47. The compartment at one end of the bore 3 incorporates the opening 5 through which sterilant can enter the challenge device, and the compartment at the other end of the bore 3 incorporates the sensor 7. Additional temperature sensors could be provided, either in that same compartment or in one or more of the other compartments 47, as required. The challenge device shown in FIG. 6 will function in a similar manner to those shown in FIGS. 1 to 5 but will offer different operating characteristics.

As an alternative to the linear arrangement of compartments 47 shown in FIG. 6, the compartments could be arranged one inside another, with the opening 5 for sterilant being located in a compartment on the outside of the arrangement and the sensor 7 being located in a compartment at the centre of the arrangement. Each compartment should be thermally-insulated individually so that the transfer of heat from the opening 5 to the sensor 7 takes place through the free space in the compartments rather than through the walls of the compartments.

In each of the challenge devices shown in FIGS. 1 to 6, the required thermal properties of the internal bore or chamber 3 are provided by walls of a single insulating material. It would, however, be possible to provide equivalent thermal properties with walls of composite construction, which may include thermally-conductive materials as well as thermally-insulating materials. For example, a challenge device of the type shown in FIGS. 1 and 2 could have one or more portions formed from a material having a relatively high thermal conductivity in combination with the thermally-insulating material to provide the required thermal properties. When material having a relatively-high thermal conductivity is present, care should be taken to ensure that it does not result in any substantial increase in heat transfer in the longitudinal direction along the walls of the bore 3. Alternatively, in the case of a challenge device of the type shown in FIG. 6, it may be possible to achieve the required thermal properties through the use of a thermally-insulating material for the walls of the compartments 47 in combination with heat sinks (high thermal capacity masses) within the compartments, provided that the free space separating the sensor 7 from the bore opening 5 is retained and is not so constricted that it could be blocked by condensate during a sterilization cycle.

Figure 10:
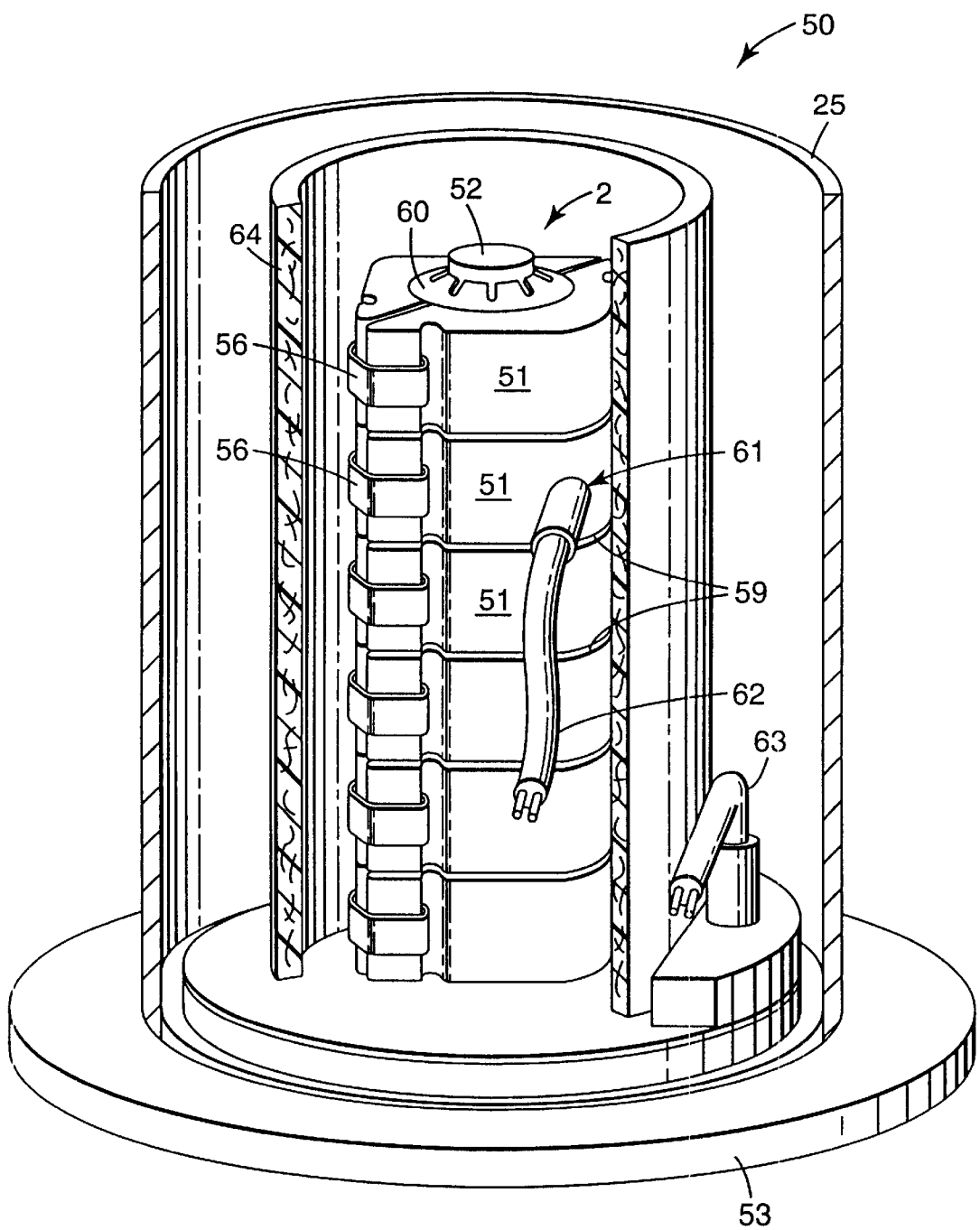
FIG. 10 is a perspective view, partly cut away, of another sterilant challenge device in accordance with the invention.

FIG. 10 illustrates a challenge device 50 which is generally similar to the device 19 shown in FIG. 4 except that the thermally-insulating wall of the tube 2 is surrounded by a plurality of thermally-conductive blocks 51 located side-by-side along the length of the tube. As in FIG. 4, the challenge device 50 is provided with a surrounding outer casing 25 which is shown, in FIG. 10, as being open-ended but which, in use, would be provided with an end plate corresponding to the end cap 23 of FIG. 4 to provide a hermetic seal. Only the closed end 52 of the tube 2 is visible in FIG. 10. Access to the bore 3 within the tube 2 is provided through an end plate 53 which surrounds the open end of the tube and supports both the thermally-conductive blocks 51 and the outer casing 25. An optional thermally-insulating cylinder 64 of open-cell foam material may be located around the thermally-conductive blocks 51, inside the outer casing 25.

Figure 11:
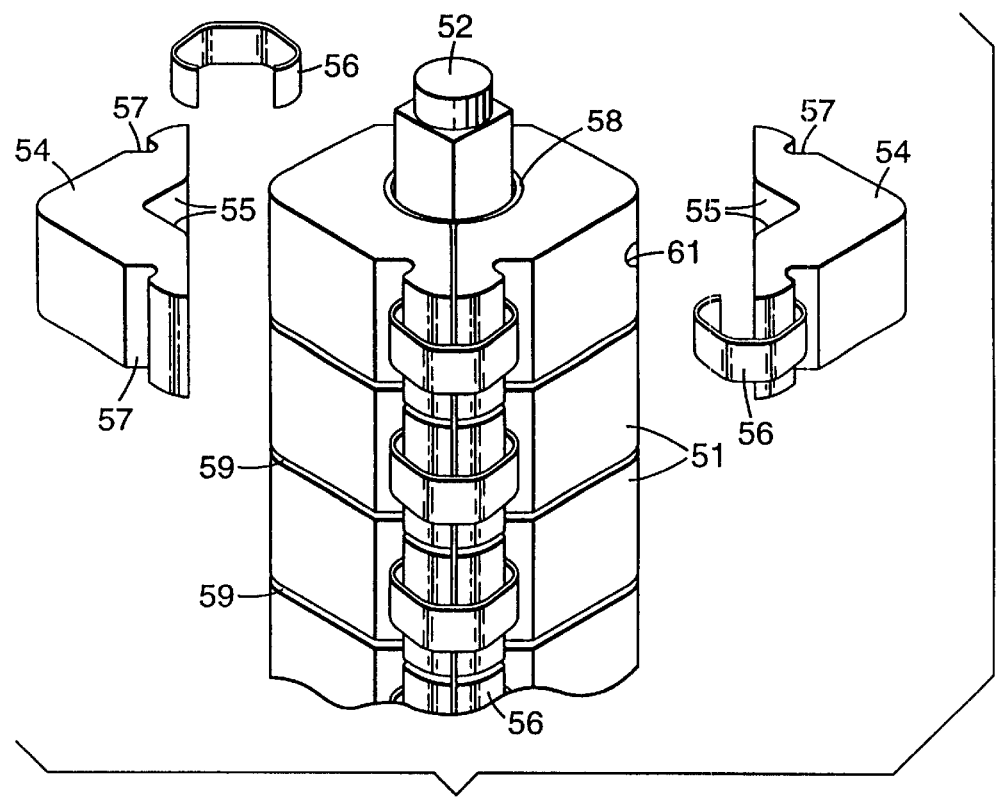
FIG. 11 is a perspective view, partly exploded, of a component of the device of FIG. 10.
Figure 12:
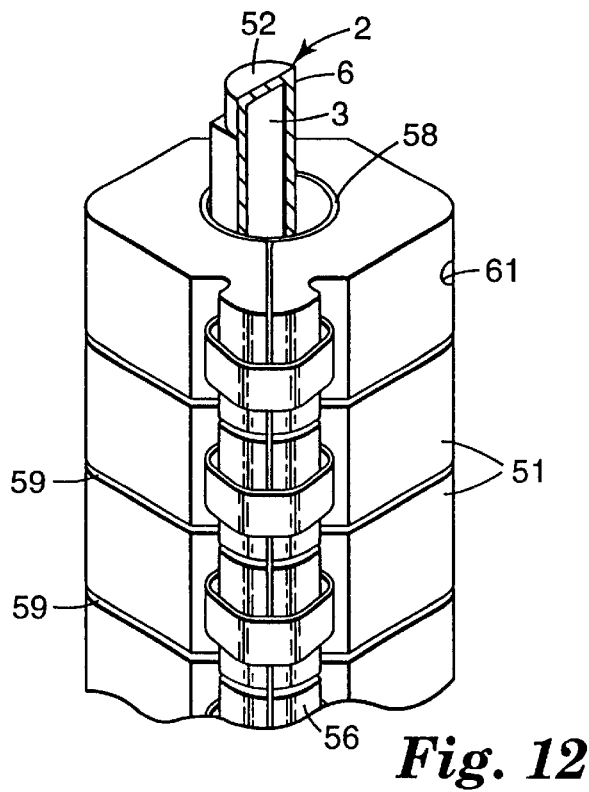
FIG. 12 is a view similar to FIG. 11 but partly in cross-section.

The construction of the device 50 (in particular the construction of the tube 2 and the blocks 51) will now be described in greater detail with reference to FIGS. 11 and 12 which show a portion only of the device, towards the closed end of the tube 2. The block 51 immediately adjacent the closed end 52 of the tube 2 is shown removed in FIG. 11 and has been omitted completely from FIG. 12.

The bore 3 of the tube 2 (visible in FIG. 12) of the circular cross-section but the outer cross-section of the tube, except immediately adjacent the closed end 52, is square. The thermally-conductive blocks 51, which form a heat sink portion of the device, are positioned on the square-sectioned part of the tube 2, each block being formed in two halves 54 having flat inner surfaces 55 corresponding to two of the outer sides of the tube. When in position on the tube 2, the two halves 54 of each block 51 are held together by two spring clips 56 which engage in recesses 57 in the outer surfaces of the block. The square outer shape of the tube 2 and the corresponding shape of the inside of the blocks 51 provides good thermal contact between the tube and the blocks and the spring clips 56 ensure that the good thermal contact is maintained while accommodating the different rates of expansion/contraction of the tube and the blocks when the challenge device 50 is in use in a sterilization chamber.

Although the blocks 51 are located side-by-side along the length of the tube 2, they do not contact one another but are spaced apart slightly by thermally-insulating O-rings 58 (one of which is visible in FIG. 11 and 12) located between adjacent blocks. The resulting air spaces 59 between the blocks cause the blocks to be themally-separated from each other and prevent heat being transmitted through the blocks along the length of the tube 2. When all the blocks 51 are in position on the tube 2, they are secured in place by a circular clip 60 (FIG. 10) fitted over the end of the tube adjacent the end block.

The penultimate block 51 on the tube 2 is formed with a circular opening 61 in which a temperature sensor, preferably a platinum resistance thermometer, (PRT), is located when the challenge device 50 is in use. The electrical leads 62 of the temperature sensor can be seen in FIG. 10. This temperature sensor replaces the temperature sensor 7 of the challenge device 19 of FIG. 4 and, unlike that temperature sensor, is not located in the bore 3 of the tube 2 but in one of the thermally-conductive blocks 51 surrounding the tube adjacent the closed end of the latter. Other forms of temperature sensor could, of course, be used.

The challenge device 50 can be used in a test pack for determining the efficacy of a sterilization cycle in the same manner as any of the challenge devices described above. In particular, the challenge device 50 can be used in a test pack of the type illustrated in FIG. 7 and comprising in addition to the challenge device, a second temperature sensor arranged to measure the temperature outside the test pack (i.e. in the sterilization chamber in which the test pack is located when in use), and the electronic circuitry of the test pack which, on the basis of the measurements from the temperature sensors, functions in the manner already described with reference to FIG. 7 to determine whether a sterilization cycle is satisfactory. With a view to use in such a test pack, the challenge device 50 is already provided with a second temperature sensor for measuring the temperature outside of the test pack and the electrical leads 63 of that second temperature sensor can be seen in FIG. 10, extending into the space between the outer casing 25 and the thermally-conductive blocks 51.

During a sterilization cycle, sterilant can enter the bore 3 of the challenge device 50 only through the lower (open) end of the tube 2. Because the tube 2 is thermally insulated from the heat in the sterilization chamber by the airspace within the casing 2 (and by the thermally-insulating cylinder 64 when present), and because the walls 6 of the bore 3 are formed from a thermally-insulating material, the bore 3 will receive heat primarily from sterilant entering the bore. As a result, that the temperature of the walls 6 will remain below that of the sterilization chamber and sterilant which enters the bore will condense on the walls 6 and not penetrate immediately to the end of the bore 3, resulting in an accumulation of air or non-condensable gas within the bore. The challenge device 50, like the other challenge devices described above, is used in the orientation shown in the drawing i.e. with the open end of the bore 3 directed downwards so that any condensate which forms within the bore during a sterilization cycle can drain away. The pocket of air or non-condensable gas which forms within the bore 3 will inhibit the penetration of sterilant to the end of the bore and will influence the temperature at the closed end of the tube 2 and in the surrounding thermally-conductive blocks 51. In this respect, it will be noted that the blocks 51 are prevented from transmitting heat to one another by the presence of the air gaps 59. Accordingly, by measuring the temperature of the blocks 51 at the closed end of the tube 2 in relation to the temperature within the sterilization chamber, it can be determined if sterilant has penetrated to the end of the tube (indicating that the sterilization cycle has been effective) or if a pocket of air or non-condensable gas remains at the end of the tube (indicating that the sterilization cycle has not been effective).

The thermally-insulating material from which the tube 2 is formed should be steam tight, and stable under the conditions encountered in a sterilization chamber.

Preferably, the thermally-insulating material is a Liquid Crystal Polymer (LCP), most preferably a complete aromatic copolyester with a 25% by weight graphite content. The thermally-conductive material from which the blocks 51 are formed is preferably aluminium. The O-rings 58 between the blocks may be formed from rubber and the outer casing 25 of the device may be formed from stainless steel. The tube 2 is typically about 115 mm long, with an internal (i.e. bore) diameter of about 6 mm and an external dimension of about 10 mm square. The blocks 51 are typically about 28 mm square, and about 15 mm wide. Six such blocks are used, as shown in the drawing, with a spacing 59 of about 1 mm between adjacent blocks. Alternatively, a larger number of thinner blocks could be used (for example, twelve blocks with a width of 7 mm).

It will be appreciated that any of the challenge devices shown in FIGS. 3 to 6 and 10 could be used in the test pack of FIG. 7 (rather than the device of FIGS. 1 and 2). Likewise, it is not only the challenge device of FIG. 4 that can be used as illustrated in FIGS. 8 and 9: any of the other challenge devices described could be used in that way.

Generally, it has been found that challenge devices of the type shown in the drawings have a somewhat delayed reaction to the changing conditions that exist in a sterilization chamber during a sterilization cycle. This is believed to be of importance when a challenge device is employed in a test pack which issues a simple "pass/fail" decision on the efficacy of a sterilization cycle since the decision will be based on conditions in a later stage of the cycle, rather than an initial stage. It has been found, particularly when a challenge device of the type shown in FIG. 10 is used, that a reliable "pass/fail" decision can be made on the basis of temperature measurements only and that humidity measurements are not essential. This is considered to be advantageous, given the much wider availability of highly reliable temperature sensors. Moreover, in the device of FIG. 10 in particular it has been found that the exact location of the sensor is not critical in enabling a reliable "pass/fail" decision to be made.

Although the challenge devices of FIGS. 1 to 6 and 10 are shown in the orientation which is preferred because it allows condensate to drain from the bore 3, that orientation is not essential. As a further modification, some form of moisture-absorbing material may be provided on the walls of the bore.

Also, although the above description refers to the challenge devices being located within a sterilization chamber for use, that is likewise not essential. Challenge devices of the type described above could be located outside a sterilizer (for example, attached to the drain line) with the open end 5 of the bore 3 being in communication through a suitable connection with the interior of the sterilization chamber.

What is claimed is:

1. A sterilant challenge device for use in a sterilizer for determining the efficacy of the air removal stage of a sterilization cycle, the sterilizer having a sterilization chamber for receiving objects to be sterilized, the sterilant challenge device comprising an exterior, walls that define a chamber that defines a remote interior space with a closed end; an opening for the entry of sterilant to the remote interior space, the opening being spaced from the closed end; a heat sink portion which, when the device is in use in a sterilizer, receives heat preferentially from the remote interior space; and a first temperature sensor for detecting the presence of sterilant at a predetermined location within the remote interior space, said predetermined location being spaced from the opening and substantially adjacent the closed end, the walls of the chamber comprising a thermally insulating material which impedes the transmission of heat from within the sterilizer to the remote interior space through the walls of the chamber, wherein the chamber is sized and shaped so that i) the penetration of sterilant from the opening to the predetermined location during a sterilization cycle is inhibited by the accumulation of air and/or non-condensable gas within the remote interior space resulting from the condensation of moisture on the walls of the chamber, and ii) there is a portion of the chamber between the opening and the predetermined location and that portion of the chamber is free of any physical barrier to the passage of the sterilant and/or air, and iii) the portion of the chamber between the opening and the predetermined location resists blockage due to condensate;

a second temperature sensor in direct thermal communication with the interior of the sterilization chamber to read the temperature of the sterilization chamber of the sterilizer, and processing means for receiving signals from said first and second temperature sensors and for making a determination of the adequacy of the sterilization cycle, based, at least in part, on the signals from said first and second temperature sensors.

2. A device as claimed in claim 1, in which the chamber is formed within the heat sink portion.

3. A device as claimed in claim 1, in which the heat sink portion is surrounded by a thermally-insulating portion whereby, during a sterilization cycle, the heat sink portion will receive heat preferentially from the remote interior space.

4. A device as claimed in claim 3, in which the thermally-insulating portion comprises an outer casing which surrounds and is spaced from the heat sink, the space containing a thermally-insulating material.

5. A device as claimed in claim 3, in which the thermally-insulating portion comprises an outer casing which surrounds, and is separated by an air space from, the heat sink.

6. A device as claimed in claim 1, in which the passageway comprises a plurality of interconnected compartments, the opening for the entry of sterilant being in one of the interconnected compartments, and the predetermined location being in another.

7. A device as claimed in claim 1, in which the passageway is the bore in a tube of thermally-insulating material, and in which the heat sink portion comprises a thermally-conductive mass located around the tube.

8. A device as claimed in claim 7, in which the heat sink portion comprises a plurality of thermally-conductive masses located around the tube along the length of the latter, the masses being thermally-separated from each other.

9. A device as claimed in claim 8, wherein the first sensor is a temperature sensor positioned to detect the temperature in one of the thermally-conductive masses at, or adjacent, the closed end of the tube, and thereby to detect the presence of sterilant in the adjacent region of the bore of the tube.

10. A sterilant challenge device for use in a steam sterilizer for determining the efficacy of the air removal stage of a sterilization cycle, the sterilizer having a sterilization chamber for receiving objects to be sterilized, the device comprising an exterior, a tube of thermally-insulating material having a length and a bore, the bore of the tube defining a remote interior space which is open at one end for the entry of sterilant and is closed at the other end; a plurality of thermally-conductive masses located around the tube, along the length of the tube, the masses being thermally-separated from one another; and thermal insulation surrounding the thermally-conductive masses, said tube being sized and shaped so that i) the penetration of steam along the bore of the tube during a sterilization cycle is inhibited through the accumulation of air and/or non-condensable gas within the remote interior space resulting from the condensation of moisture on the bore, the device also comprising a first temperature sensor to detect the presence of steam, the first temperature sensor being located at, or adjacent, the closed end of the tube and a second temperature sensor in direct thermal communication with the interior of the sterilization chamber to read the temperature of the sterilization chamber of the sterilizer, wherein the tube is sized and shaped so that there is a portion of the tube between the opening and the first temperature sensor and that portion of the tube is free of any physical barrier to the passage of the steam and/or air and that portion of the tube is sized and shaped to resist blockage due to condensate, and processing means for receiving signals from said first and second temperature sensors and for making a determination of the adequacy of the sterilization cycle.

11. A device as claimed in claim 10, wherein the first temperature sensor is located in one of the thermally-conductive masses at, or adjacent, the closed end of the tube, to detect the temperature in the thermally-conductive mass and thereby detect the presence of sterilant in the adjacent region of the bore of the tube.

12. A device as claimed in claim 10, in which the thermal insulation surrounding and thermally-conductive masses is provided by an outer casing which surrounds and thermally-conductive masses and is separated therefrom by an air space.

* * * * *

UNITED STATES PATENT AND TRADEMARK OFFICE
CERTIFICATE OF CORRECTION

PATENT NO. : 6,323,032 B1   Page 1 of 1
DATED : November 27, 2001
INVENTOR(S) : Anton Kuepper and Brian Kirk It is certified that error appears in the above-identified patent and that said Letters Patent is hereby corrected as shown below:

<u>Title page,</u>
ABSTRACT, second line, before the word "removal" insert -- air --.

<u>Column 1,</u>
Line 12, delete the word "stem" and insert in place thereof -- systems --.

<u>Column 5,</u>
Line 15, delete the word "diode" and insert in place thereof -- diagrammatic --.

Signed and Sealed this

Twenty-first Day of May, 2002

*Attest:*

*Attesting Officer*

JAMES E. ROGAN
*Director of the United States Patent and Trademark Office*